(12) United States Patent
Borgert et al.

(10) Patent No.: US 8,971,988 B2
(45) Date of Patent: Mar. 3, 2015

(54) ARRANGEMENT AND METHOD FOR INFLUENCING AND/OR DETECTING MAGNETIC PARTICLES

(75) Inventors: Joern Borgert, Hamburg (DE); Bernhard Gleich, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 545 days.

(21) Appl. No.: 13/320,823

(22) PCT Filed: May 12, 2010

(86) PCT No.: PCT/IB2010/052111
§ 371 (c)(1),
(2), (4) Date: Nov. 16, 2011

(87) PCT Pub. No.: WO2010/134006
PCT Pub. Date: Nov. 25, 2010

(65) Prior Publication Data
US 2012/0065491 A1 Mar. 15, 2012

(30) Foreign Application Priority Data

May 18, 2009 (EP) .................................... 09160510

(51) Int. Cl.
*A61B 5/05* (2006.01)
*G01R 33/12* (2006.01)
*G01N 27/72* (2006.01)
(Continued)

(52) U.S. Cl.
CPC ................. *A61B 5/05* (2013.01); *A61B 5/0515* (2013.01); *A61B 5/6814* (2013.01); *A61N 1/406* (2013.01)
USPC .......................................... 600/409; 328/228

(58) Field of Classification Search
USPC .......... 600/407, 409, 420, 422–425; 324/204, 324/228, 307, 318; 607/105; 73/53.01; 702/57
See application file for complete search history.

(56) References Cited

U.S. PATENT DOCUMENTS 5,372,137 A * 12/1994 Wong et al. ................... 600/422
2002/0016533 A1 2/2002 Marchitto et al.
(Continued)

FOREIGN PATENT DOCUMENTS

DE 10151778 A1 10/2001
EP 1304542 A2 4/2003
(Continued)

OTHER PUBLICATIONS

Timo F Sattel et al: Fast Track Communication; "Single-Sided Device for Magneitic Particle Imaging" Journal of Physics D. Applied Physics, IOP Publishing, Bristol, GB XP020149056 ISSN: 0022-3727 vol. 42, No. 2, Jan. 21, 2009, p. 1-5.
(Continued)

*Primary Examiner* — Long V Le
*Assistant Examiner* — Lawrence Laryea

(57) ABSTRACT

The present invention relates to an arrangement and a method for influencing and/or detecting magnetic particles in a region of action, in particular for monitoring of intra-cerebral or intra-cranial bleeding using Magnetic Particle Imaging (MPI). A common coupling unit per coil of a coil array is provided for coupling all signals for generating the magnetic fields to the set of common coils. Further, the same coils are used for acquiring detection signals. In this way a small scanner can be built that can be left permanently or can be provided periodically to the patient, in particular for bleeding monitoring.

17 Claims, 7 Drawing Sheets

(51) Int. Cl.
*A61B 5/00* (2006.01)
*A61N 1/40* (2006.01)

(56) References Cited

U.S. PATENT DOCUMENTS

| | | | |
|---|---|---|---|
| 2005/0083057 A1* | 4/2005 | Schulz et al. | 324/318 |
| 2008/0007250 A1 | 1/2008 | Wiggins | |
| 2008/0204009 A1* | 8/2008 | Gleich et al. | 324/228 |
| 2008/0294035 A1 | 11/2008 | Zwick et al. | |

FOREIGN PATENT DOCUMENTS

JP  2009056232 A  3/2009

WO  2008078244 A2  7/2008

OTHER PUBLICATIONS

J. Weizenecker et al: "Three-Dimensional Real-Time In Vivo Magnetic Particle Imaging" Letter to the Editor; Physics in Medicine and Biology, vol. 54, No. 5, Mar. 7, 2009. XP020149861 ISSN: 0031-9155, pp. L1-L10.

A. Antonelli et al.: "New Biomimetic Constructs for Improved In Vivo Circulation of Superparamagnetic Nanoparticles" Journal of Nanoscience and Nanotechnology, vol. 8., 2008, pp. 2270-2278.

B. Gleich et al.,: "Tomographic Imaging Using the Nonlinear Response of Magnetic Particles" in nature, vol. 435, Jun. 30, 2005, pp. 1214-1217.

* cited by examiner

ARRANGEMENT AND METHOD FOR INFLUENCING AND/OR DETECTING MAGNETIC PARTICLES

FIELD OF THE INVENTION

The present invention relates to an arrangement and a method for influencing and/or detecting magnetic particles in a region of action. Further, the present invention relates to an arrangement and a method for detecting magnetic particles in a region of action and for bleeding monitoring. Still further, the present invention relates to a computer program for implementing said methods on a computer and to control such an arrangement.

The invention relates particularly to the detection of intra-cerebral and intra-cranial bleeding.

BACKGROUND OF THE INVENTION

An arrangement of this kind is known from German patent application DE 101 51 778 A1. In the arrangement described in that publication, first of all a magnetic selection field having a spatial distribution of the magnetic field strength is generated such that a first sub-zone having a relatively low magnetic field strength and a second sub-zone having a relatively high magnetic field strength are formed in the examination zone. The position in space of the sub-zones in the examination zone is then shifted, so that the magnetization of the particles in the examination zone changes locally. Signals are recorded which are dependent on the magnetization in the examination zone, which magnetization has been influenced by the shift in the position in space of the sub-zones, and information concerning the spatial distribution of the magnetic particles in the examination zone is extracted from these signals, so that an image of the examination zone can be formed. Such an arrangement has the advantage that it can be used to examine arbitrary examination objects—e.g. human bodies—in a non-destructive manner and without causing any damage and with a high spatial resolution, both close to the surface and remote from the surface of the examination object.

A similar arrangement and method is known from Gleich, B. and Weizenecker, J. (2005), "Tomographic imaging using the nonlinear response of magnetic particles" in nature, vol. 435, pp. 1214-1217. The arrangement and method for magnetic particle imaging (MPI) described in that publication takes advantage of the non-linear magnetization curve of small magnetic particles.

Intra-cerebral or intra-cranial bleedings can be detected in situ during a normal diagnostic scan with established imaging modalities, like CT or MRI. This is general practice during the differential diagnosis of neurological incidents to allow for the distinction between ischemic stroke and bleeding. This, however, rules out patients who need constant monitoring for bleeding, e.g. after a dissection of a cerebral or cranial arterial or patients that undergo lysis therapy where one of the major complications is the occurrence of spontaneous bleeding.

The commonly known modalities used for medical imaging that can be used to detect bleeding, e.g. MRI (Magnetic Resonance Imaging) or CT (Computed Tomography), are only available for a limited amount of time, e.g. for a diagnostic scan. However, patients who need constant monitoring for bleeding need a system that is constantly available or available periodically and can be made available with very little effort.

SUMMARY OF THE INVENTION

It is an object of the present invention to provide an arrangement and a method for influencing and/or detecting magnetic particles in a region of action, as well as a method for bleeding monitoring that allow constant or periodic monitoring of a patient over a longer period of time and that can be made easily available to a patient.

In a first aspect of the present invention an arrangement for influencing and/or detecting magnetic particles in a region of action is presented comprising:

selection means comprising a selection field signal generator unit and selection field coils for generating a magnetic selection field having a pattern in space of its magnetic field strength such that a first sub-zone having a low magnetic field strength and a second sub-zone having a higher magnetic field strength are formed in the region of action, drive means comprising drive field signal generator units and drive field coils for changing the position in space of the two sub-zones in the region of action by means of a magnetic drive field so that the magnetization of the magnetic material changes locally, receiving means comprising at least one signal receiving unit and at least one receiving coil for acquiring detection signals, which detection signals depend on the magnetization in the region of action, which magnetization is influenced by the change in the position in space of the first and second sub-zone, wherein said selection field coils, said drive field coils and said at least one receiving coil are implemented by a set of common coils, and wherein said arrangement further comprises coupling means inducting a coupling unit per coil of said set of common coils coupled between the selection field signal generator unit, the drive field generator unit and the associated coil of said set of common coils.

In a further aspect of the present invention a corresponding method is presented.

Preferred embodiments of the invention are defined in the dependent claims. It shall be understood that the claimed methods have similar and/or identical preferred embodiments as the claimed arrangement and as defined in the dependent claims.

The present invention is based on the idea to use a common set of coils, i.e. a single coil array, for generation of all necessary magnetic fields, i.e. the magnetic selection field, the magnetic drive field and, if applicable, a magnetic focus field, as well as for detection of detection signals depending on the magnetization in the region of action. This becomes particularly possible by the use of a common coupling unit which is coupled between the various field signal generator units and their respective coil, i.e. for each coil of said set of common coils (also referred to as a coil array) a coupling unit is provided. In this way, the various signals for generating the various magnetic fields are merged for common control of the coils of said set of common coils.

The invention is particularly applicable when using small sized coils and when requiring small magnetic field strengths. Due to said small size and such small field strengths it is possible to build the arrangement, in particular the set of common coils, in a compact and handy way which allows it to either have it available permanently at the patient bed or make it available with very little effort by bringing it to the patient's bed periodically, e.g. mounted on a cart. Thus, for instance, a magnetic particle imaging scanner can be built that is dedicated to monitoring intra-cranial or intra-cerebral bleedings, and the scanner can be built in an open fashion, which allows comfortable and easy access to the patient while simultaneously monitoring the patient. Of course, the invention can be implemented in arrangements for other purposes, in particular for monitoring other parts of a patient, such as a heart or the abdominal region.

According to a preferred embodiment the coils of said set of coils are arranged in a common housing including a coil connector substantially made from magnetically soft material connecting said coils. Said magnetically soft material is preferably made from iron, and a coil connector preferably comprises a shielding, in particular made from copper. The coil connector provides a good direction of the magnetic flux and increases the field strength. In addition, the shielding prevents the generation of harmonics in the magnetic coil connector, mainly due to the magnetic drive fields.

According to a further embodiment the coils of said set of common coils, the housing and the coil connector are adapted for placement in close vicinity of a body part of a patient, in particular the head of a patient. The invention allows to design the essential elements that need to be placed next to the body part to be monitored such that they cover only those crucial parts and can be placed close to those parts. As mentioned above, these elements of the arrangement can be realized to reside directly on the patient bed to allow for a constant monitoring, e.g. of a bleeding, or on a cart to allow easy provision of the arrangement for periodic scanning of several different patients.

For monitoring of bleedings in the head of a patient these elements can be arranged in the form of a helmet which, for instance, can be placed on the patient bed into which the patient's head can be placed.

In a further embodiment said coil connector is arranged in the form of a half shell covering the coils of said set of common coils and comprises extensions, in particular spike-like extensions, for connection to said coils. These extensions particularly improve the magnetic flux and direct the magnetic flux to the individual coils. A further advantage is that this leads to lower power requirements.

Preferably, the coupling unit comprises a tank circuit, which is preferably adapted for simultaneous coupling of the signals generated by the field signal generator units to the coils. The tank circuit is particularly provided to serve for ensuring that the drive field signals are not short-cut to the ground so that the detection signal would not be detectable, since it would be lead to the ground.

For correct detection of detection signals acquired by one or more of the coils of said set of common coils acting as receiving coils it is proposed in a further embodiment to provide an inductive element coupled in series to the receiving coils, and to further provide a resonant circuit coupled between the coupling point of said inductive element and said receiving coil and the receiving unit associated with said receiving coil. Thus, an inductive potential divider is formed by the inductive element and the receiving coil for correctly tapping the detector signal at the coupling point there between.

In a further embodiment a control unit is provided for controlling said drive field signal generator units such that in predetermined regions the amplitude of the generated magnetic drive field does not exceed a predetermined magnetic field intensity. In this way it can be ensured that no overheating appears in said predetermined regions. For instance, the heating of potential dental fillings and orthopedic devices like braces or retainers can be minimized in this way to prevent any damage to the patient during a constant monitoring process.

In still a further aspect of the present invention an arrangement for detecting magnetic particles in a region of action and for bleeding monitoring is presented comprising a signal processing means for processing detection signals received by said signal receiving means, said signal processing means comprising:

comparing means for comparing received detection signals of a region of action to previously acquired reference signals from the same region of action, first determining means for determining, based on said comparison, areas of increased blood volume, second determining means for determining the pulsation pattern of the blood in said areas of increased blood volume, and third determining means for determining which of said areas of increased blood volume are areas with bleedings based on the determined pulsation pattern.

This aspect of the present invention is particularly directed to the monitoring of bleedings and allows determining whether a particular area which shows an increased blood volume is an area with bleedings or just shows a normal variation in the local blood volume. The main idea is to distinguish between such areas by use of a determination of the pulsation pattern of the blood in said area of increased blood volume. Regions of a normal variation (increase) in local blood volume usually show a characteristic pulsation pattern due to heartbeat, whereas areas with increased blood volume due to bleeding will have different to no pattern at all. This recognition is preferably exploited according to this aspect of the present invention.

The arrangement according to the first aspect of the present invention as explained above can be particularly applied for said monitoring of bleedings, in particular since it is able to be used for constant or periodic monitoring of a patient. For these kinds of applications the magnetic particle imaging (MPI) technology shows its advantages over the common imaging modalities.

According to another preferred embodiment the processing means further comprises registration means for registering the signals received by said signal receiving means with the reference signals for motion correction of the patient. This increases accuracy of the method.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Before the details of the present invention shall be explained, basics of magnetic particle imaging shall be explained in details with reference to FIGS. 1 to 4.

Figure 1:
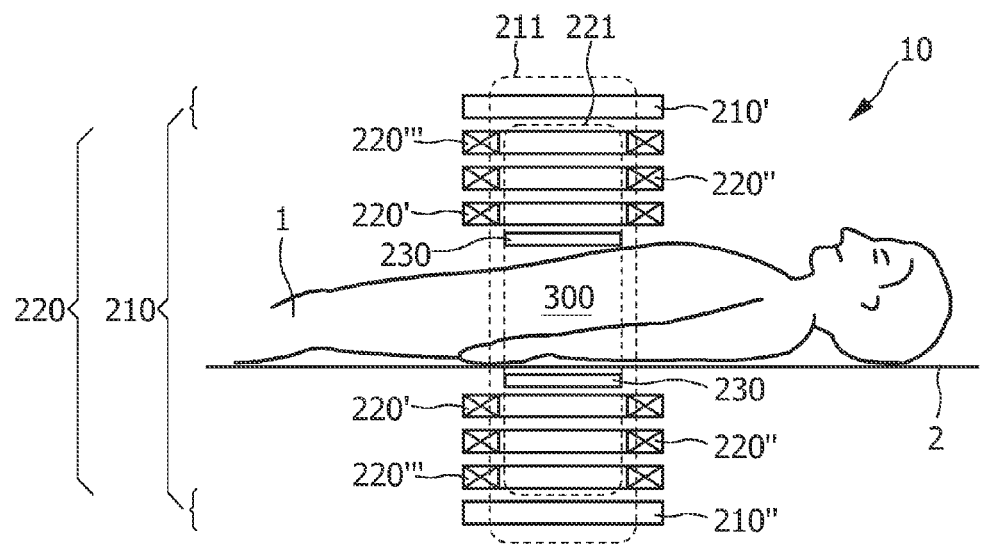
FIG. 1 shows a schematic view of the principle layout of a magnetic particle imaging (MPI) arrangement.

FIG. 1 shows an arbitrary object to be examined by means of a MPI arrangement 10. The reference numeral 1 in FIG. 1 denotes an object, in this case a human or animal patient, who is arranged on a patient table 2, only part of the top of which is shown. Prior to the application of the imaging method, magnetic particles 100 (not shown in FIG. 1) are arranged in a region of action 300 of the inventive arrangement 10. Especially prior to a therapeutic and/or diagnostic treatment of, for example, a tumor, the magnetic particles 100 are positioned in the region of action 300, e.g. by means of a liquid (not shown) comprising the magnetic particles 100 which is injected into the body of the patient 1.

Figure 2:
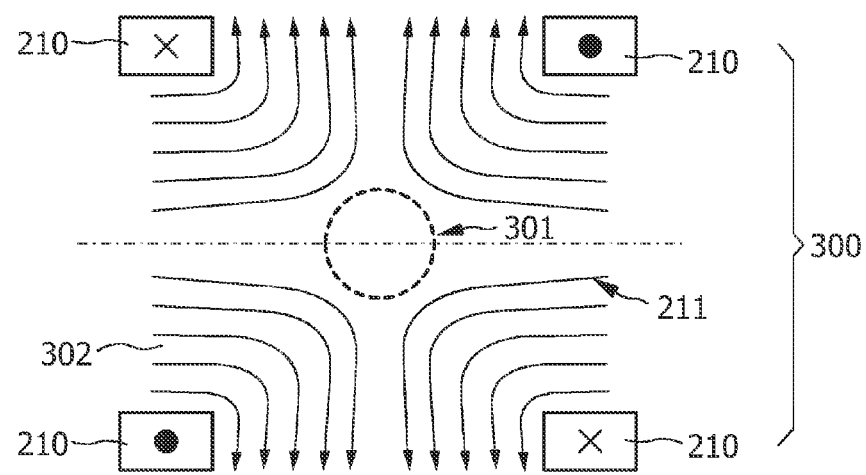
FIG. 2 shows an example of the field line pattern produced by an arrangement as shown in FIG. 1.

As an example of an arrangement of coils is shown in FIG. 2 comprising a plurality of coils forming a selection means 210 whose range defines the region of action 300 which is also called the region of treatment 300. For example, the selection means 210 is arranged above and below the patient 1 or above and below the table top. For example, the selection means 210 comprise a first pair of coils 210', 210", each comprising two identically constructed windings 210' and 210" which are arranged coaxially above and below the patient 1 and which are traversed by equal currents, especially in opposed directions. The first coil pair 210', 210" together are called selection means 210 in the following. Preferably, direct currents are used in this case. The selection means 210 generate a magnetic selection field 211 which is in general a gradient magnetic field which is represented in FIG. 2 by the field lines. It has a substantially constant gradient in the direction of the (e.g. vertical) axis of the coil pair of the selection means 210 and reaches the value zero in a point on this axis. Starting from this field-free point (not individually shown in FIG. 2), the field strength of the magnetic selection field 211 increases in all three spatial directions as the distance increases from the field-free point. In a first sub-zone 301 or region 301 which is denoted by a dashed line around the field-free point the field strength is so small that the magnetization of particles 100 present in that first sub-zone 301 is not saturated, whereas the magnetization of particles 100 present in a second sub-zone 302 (outside the region 301) is in a state of saturation. The field-free point or first sub-zone 301 of the region of action 300 is preferably a spatially coherent area; it may also be a punctiform area or else a line or a flat area. In the second sub-zone 302 (i.e. in the residual part of the region of action 300 outside of the first sub-zone 301) the magnetic field strength is sufficiently strong to keep the particles 100 in a state of saturation. By changing the position of the two sub-zones 301, 302 within the region of action 300, the (overall) magnetization in the region of action 300 changes. By measuring the magnetization in the region of action 300 or a physical parameters influenced by the magnetization, information about the spatial distribution of the magnetic particles in the region of action can be obtained. In order to change the relative spatial position of the two sub-zones 301, 302 in the region of action 300, a further magnetic field, the so-called magnetic drive field 221, is superposed to the selection field 211 in the region of action 300 or at least in a part of the region of action 300.

Figure 3:
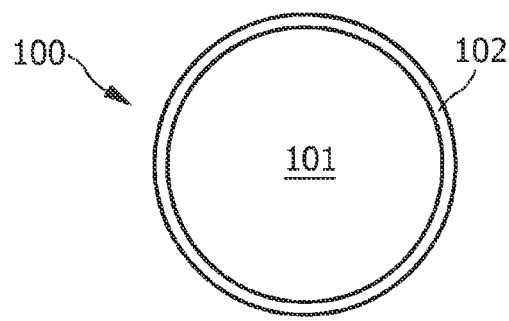
FIG. 3 shows an enlarged view of a magnetic particle present in the region of action.

FIG. 3 shows an example of a magnetic particle 100 of the kind used together with an arrangement 10 as shown above, but also according to the present invention. It comprises for example a spherical substrate 101, for example, of glass which is provided with a soft-magnetic layer 102 which has a thickness of, for example, 5 nm and consists, for example, of an iron-nickel alloy (for example, Permalloy). This layer may be covered, for example, by means of a coating layer 103 which protects the particle 100 against chemically and/or physically aggressive environments, e.g. acids. The magnetic field strength of the magnetic selection field 211 required for the saturation of the magnetization of such particles 100 is dependent on various parameters, e.g. the diameter of the particles 100, the used magnetic material for the magnetic layer 102 and other parameters.

In the case of e.g. a diameter of 10 µm, a magnetic field of approximately 800 A/m (corresponding approximately to a flux density of 1 mT) is then required, whereas in the case of a diameter of 100 µm a magnetic field of 80 A/m suffices. Even smaller values are obtained when a coating 102 of a material having a lower saturation magnetization is chosen or when the thickness of the layer 102 is reduced.

For further details of the preferred magnetic particles 100, the corresponding parts of DE 10151778 are hereby incorporated by reference, especially paragraphs 16 to 20 and paragraphs 57 to 61 of EP 1304542 A2 claiming the priority of DE 10151778.

The size of the first sub-zone 301 is dependent on the one hand on the strength of the gradient of the magnetic selection field 211 and on the other hand on the field strength of the magnetic field required for saturation. For a sufficient saturation of the magnetic particles 100 at a magnetic field strength of 80 A/m and a gradient (in a given space direction) of the field strength of the magnetic selection field 211 amounting to 160 $10^3$ A/m2, the first sub-zone 301 in which the magnetization of the particles 100 is not saturated has dimensions of about 1 mm (in the given space direction).

When a further magnetic field—in the following called a magnetic drive field 221 is superposed on the magnetic selection field 210 (or gradient magnetic field 210) in the region of action 300, the first sub-zone 301 is shifted relative to the second sub-zone 302 in the direction of this magnetic drive field 221; the extent of this shift increases as the strength of the magnetic drive field 221 increases. When the superposed magnetic drive field 221 is variable in time, the position of the first sub-zone 301 varies accordingly in time and in space. It is advantageous to receive or to detect signals from the magnetic particles 100 located in the first sub-zone 301 in another frequency band (shifted to higher frequencies) than the frequency band of the magnetic drive field 221 variations. This is possible because frequency components of higher harmonics of the magnetic drive field 221 frequency occur due to a change in magnetization of the magnetic particles 100 in the region of action 300 as a result of the non-linearity of the magnetization characteristics.

In order to generate these magnetic drive fields 221 for any given direction in space, there are provided three further coil pairs, namely a second coil pair 220', a third coil pair 220" and a fourth coil pair 220'" which together are called drive means 220 in the following. For example, the second coil pair 220' generates a component of the magnetic drive field 221 which extends in the direction of the coil axis of the first coil pair 210', 210" or the selection means 210, i.e. for example vertically. To this end the windings of the second coil pair 220' are traversed by equal currents in the same direction. The effect that can be achieved by means of the second coil pair 220' can in principle also be achieved by the superposition of currents in the same direction on the opposed, equal currents in the first coil pair 210', 210", so that the current decreases in one coil and increases in the other coil. However, and especially for the purpose of a signal interpretation with a higher signal to noise ratio, it may be advantageous when the temporally constant (or quasi constant) selection field 211 (also called gradient magnetic field) and the temporally variable vertical magnetic drive field are generated by separate coil pairs of the selection means 210 and of the drive means 220.

The two further coil pairs 220", 220''' are provided in order to generate components of the magnetic drive field 221 which extend in a different direction in space, e.g. horizontally in the longitudinal direction of the region of action 300 (or the patient 1) and in a direction perpendicular thereto. If third and fourth coil pairs 220", 220''' of the Helmholtz type (like the coil pairs for the selection means 210 and the drive means 220) were used for this purpose, these coil pairs would have to be arranged to the left and the right of the region of treatment or in front of and behind this region, respectively. This would affect the accessibility of the region of action 300 or the region of treatment 300. Therefore, the third and/or fourth magnetic coil pairs or coils 220", 220''' are also arranged above and below the region of action 300 and, therefore, their winding configuration must be different from that of the second coil pair 220'. Coils of this kind, however, are known from the field of magnetic resonance apparatus with open magnets (open MRI) in which an radio frequency (RF) coil pair is situated above and below the region of treatment, said RF coil pair being capable of generating a horizontal, temporally variable magnetic field. Therefore, the construction of such coils need not be further elaborated herein.

The arrangement 10 further comprises receiving means 230 that are only schematically shown in FIG. 1. The receiving means 230 usually comprise coils that are able to detect the signals induced by magnetization pattern of the magnetic particles 100 in the region of action 300. Coils of this kind, however, are known from the field of magnetic resonance apparatus in which e.g. a radio frequency (RF) coil pair is situated around the region of action 300 in order to have a signal to noise ratio as high as possible. Therefore, the construction of such coils need not be further elaborated herein.

In an alternative embodiment for the selection means 210 shown in FIG. 1, permanent magnets (not shown) can be used to generate the gradient magnetic selection field 211. In the space between two poles of such (opposing) permanent magnets (not shown) there is formed a magnetic field which is similar to that of FIG. 2, that is, when the opposing poles have the same polarity. In another alternative embodiment of the arrangement, the selection means 210 comprise both at least one permanent magnet and at least one coil 210', 210" as depicted in FIG. 2.

The frequency ranges usually used for or in the different components of the selection means 210, drive means 220 and receiving means 230 are roughly as follows: The magnetic field generated by the selection means 210 does either not vary at all over the time or the variation is comparably slow, preferably between approximately 1 Hz and approximately 100 Hz. The magnetic field generated by the drive means 220 varies preferably between approximately 25 kHz and approximately 100 kHz. The magnetic field variations that the receiving means are supposed to be sensitive are preferably in a frequency range of approximately 50 kHz to approximately 10 MHz.

Figure 4A:
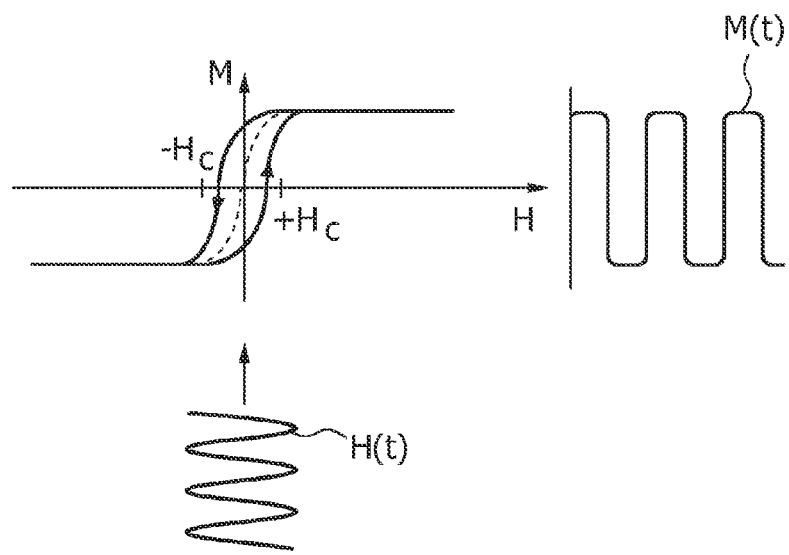
FIGS. 4a and 4b show the magnetization characteristics of such particles.
Figure 4B:
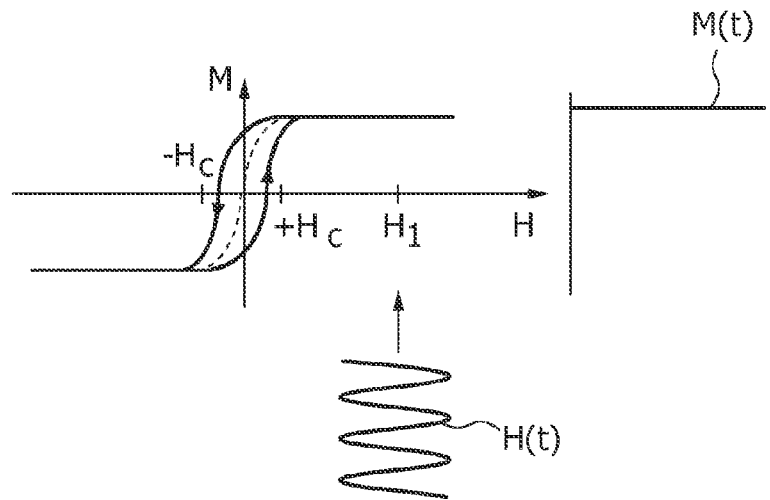

FIGS. 4a and 4b show the magnetization characteristic, that is, the variation of the magnetization M of a particle 100 (not shown in FIGS. 4a and 4b) as a function of the field strength H at the location of that particle 100, in a dispersion with such particles. It appears that the magnetization M no longer changes beyond a field strength $+H_c$ and below a field strength $-H_c$, which means that a saturated magnetization is reached. The magnetization M is not saturated between the values $+H_c$ and $-H_c$.

FIG. 4a illustrates the effect of a sinusoidal magnetic field H(t) at the location of the particle 100 where the absolute values of the resulting sinusoidal magnetic field H(t) (i.e. "seen by the particle 100") are lower than the magnetic field strength required to magnetically saturate the particle 100, i.e. in the case where no further magnetic field is active. The magnetization of the particle 100 or particles 100 for this condition reciprocates between its saturation values at the rhythm of the frequency of the magnetic field H(t). The resultant variation in time of the magnetization is denoted by the reference M(t) on the right hand side of FIG. 4a. It appears that the magnetization also changes periodically and that the magnetization of such a particle is periodically reversed.

The dashed part of the line at the centre of the curve denotes the approximate mean variation of the magnetization M(t) as a function of the field strength of the sinusoidal magnetic field H(t). As a deviation from this centre line, the magnetization extends slightly to the right when the magnetic field H increases from $-H_c$ to $+H_c$ and slightly to the left when the magnetic field H decreases from $+H_c$ to $-H_c$. This known effect is called a hysteresis effect which underlies a mechanism for the generation of heat. The hysteresis surface area which is formed between the paths of the curve and whose shape and size are dependent on the material, is a measure for the generation of heat upon variation of the magnetization.

FIG. 4b shows the effect of a sinusoidal magnetic field H(t) on which a static magnetic field $H_1$ is superposed. Because the magnetization is in the saturated state, it is practically not influenced by the sinusoidal magnetic field H(t). The magnetization M(t) remains constant in time at this area. Consequently, the magnetic field H(t) does not cause a change of the state of the magnetization.

Figure 5:
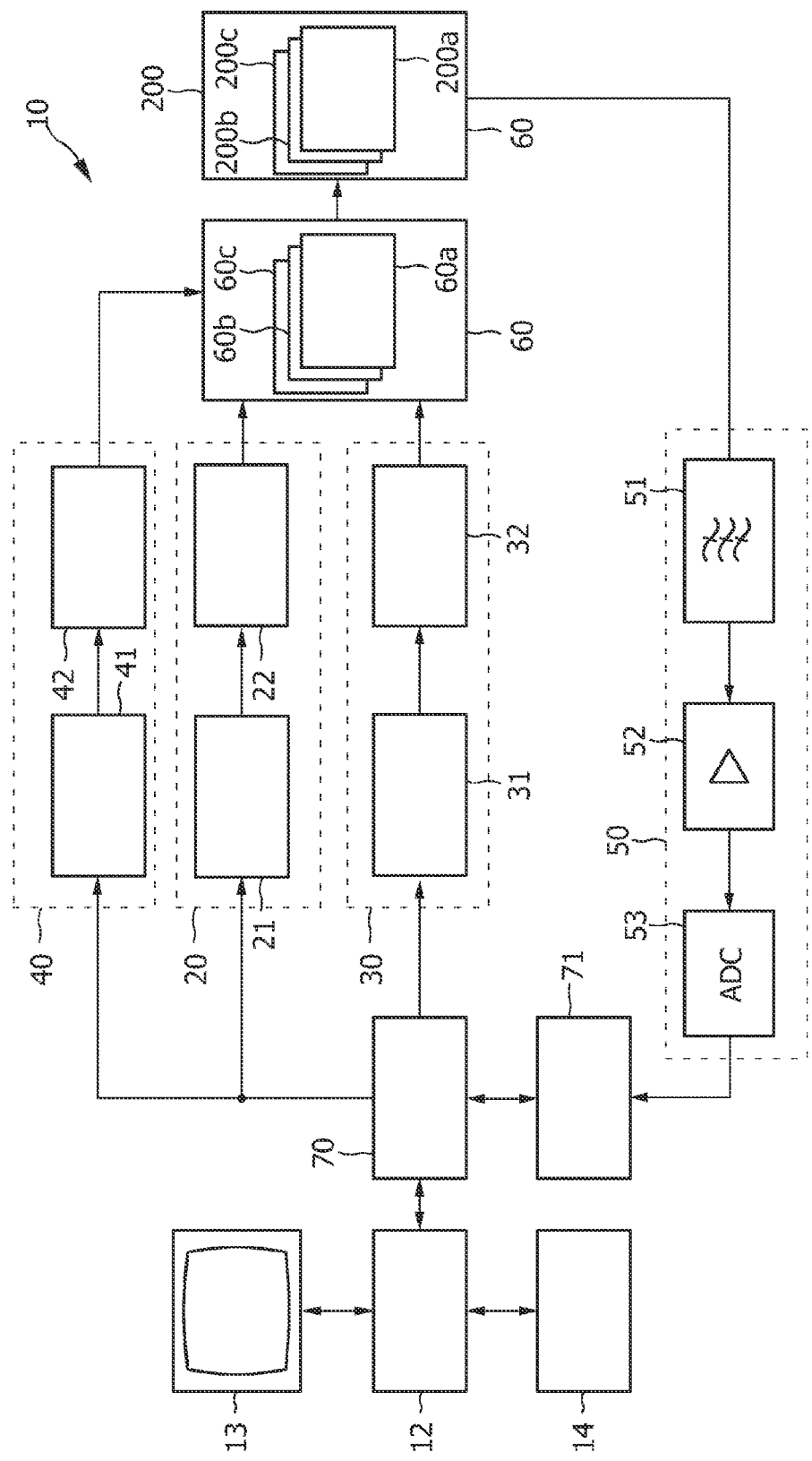
FIG. 5 shows a block diagram of the arrangement according to the present invention, FIG. 6 schematically illustrates the implementation of an arrangement according to the present invention in a cart, FIG. 7 schematically illustrates another implementation of the coils of an arrangement according to the present invention as head coils, FIG. 8 schematically illustrates the implementation of the coils of an arrangement according to the present invention as a kind of helmet.

FIG. 5 shows a block diagram of an embodiment of the apparatus 10 according to the present invention. The general principles of magnetic particle imaging explained above are valid and applicable here as well, unless otherwise specified.

The embodiment of the apparatus 10 shown in FIG. 5 comprises a set 200 of three common coils 200a, 200b, 200c which serve for generating all necessary magnetic fields and for signal detection as will be explained below. For generating the magnetic selection field explained above a selection field signal generator unit 20 is provided, preferably for each coil 200a, 200b, 200c of the set 200 that shall be used as a selection field coil a separate selection field signal generator unit 20 is provided (although it is generally also possible to provide a single common selection field signal generator unit 20 for all selection field coils). Said selection field signal generator unit 20 comprises a controllable selection field current source 21 (generally including an amplifier) and a filter unit 22 which provide the respective section field coil with the selection field current to individually set the gradient strength of the selection field in the desired direction. Preferably, a DC current is provided. If the selection field coils are arranged as opposed coils, e.g. on opposite sides of the region of action, the selection field currents of opposed coils are preferably oppositely oriented.

The selection field signal generator unit 20 is controlled by a control unit 70, which preferably controls the selection field current generation such that the sum of the field strength and the sum of the gradient strength of all spatial fractions of the selection field is maintained at a predefined level.

For generation of the magnetic drive field the apparatus 10 further comprises a drive field signal generator unit 30, preferably a separate drive field signal generation unit for each coil of said set 200 that shall be used for drive field generation. Said drive field signal generator unit 30 comprises a drive field current source 31 (preferably including a current amplifier) and a filter unit 32 for providing a drive field current to the respective drive field coil. The drive field current source 31 is adapted for generating an AC current and is also controlled by the control unit 70.

Preferably (but not necessarily), the apparatus 10 further comprises a focus field signal generator unit 40 comprising a focus field current source 41 (preferably comprising a current amplifier) and a filter unit 42 for providing a focus field current to the respective coil of said set 200 of coils which shall be used for generating a magnetic focus field. Said magnetic focus field is generally used for changing the position in space of the region of action as is generally known in the art of MPI.

For signal detection a signal receiving unit 50 is provided which receives signals detected by a coil 200a, 200b, 200c of said set 200 that is used for signal detection. Preferably, for each coil of said set which shall be used as a signal receiving coil a separate signal receiving unit 50 is provided. Said signal receiving unit 50 comprises a filter unit 51 for filtering the received detection signals. The aim of this filtering is to separate measured values, which are caused by the magnetization in the examination area which is influenced by the change in position of the two part-regions (301, 302), from other, interfering signals. To this end, the filter unit 51 may be designed for example such that signals which have temporal frequencies that are smaller than the temporal frequencies with which the coils 200a, 200b, 200c are operated, or smaller than twice these temporal frequencies, do not pass the filter unit 51. The signals are then transmitted via an amplifier unit 52 to an analog/digital converter 53 (ADC). The digitalized signals produced by the analog/digital converter 53 are fed to an image processing unit (also called reconstruction means) 71, which reconstructs the spatial distribution of the magnetic particles from these signals and the respective position which the first part-region 301 of the first magnetic field in the examination area assumed during receipt of the respective signal and which the image processing unit 71 obtains from the control unit 70. The reconstructed spatial distribution of the magnetic particles is finally transmitted via the control means 70 to a computer 12, which displays it on a monitor 13. Thus, an image can be displayed showing the distribution of magnetic particles in the examination area.

Further, an input unit 14 is provided, for example a keyboard. A user is therefore able to set the desired direction of the highest resolution and in turn receives the respective image of the region of action on the monitor 13. If the critical direction, in which the highest resolution is needed, deviates from the direction set first by the user, the user can still vary the direction manually in order to produce a further image with an improved imaging resolution. This resolution improvement process can also be operated automatically by the control unit 70 and the computer 12. The control unit 70 in this embodiment sets the gradient field in a first direction which is automatically estimated or set as start value by the user. The direction of the gradient field is then varied stepwise until the resolution of the thereby received images, which are compared by the computer 12, is maximal, respectively not improved anymore. The most critical direction can therefore be found respectively adapted automatically in order to receive the highest possible resolution.

The apparatus 10 further comprises a coupling means 60 including a coupling unit 60a, 60b, 60c per coil 200a, 200b, 200c of said set 200 of common coils. Said coupling means 60 are coupled between the selection field signal generator unit 20, the drive field generator unit 30, the focus field signal generator unit 40 (if present), and the associated coil 200a, 200b, 200c of said set 200 of common coils. The coupling means 60 are adapted for merging the various signals required for generation of the magnetic fields, which is generally possible for all coils sizes and magnetic field strengths. But this is particularly advantageous, especially in view of the required power and cooling, if the coils have a small size and if small magnetic field strengths are required. An embodiment of such a coupling unit will be explained below in more detail.

Figure 6:
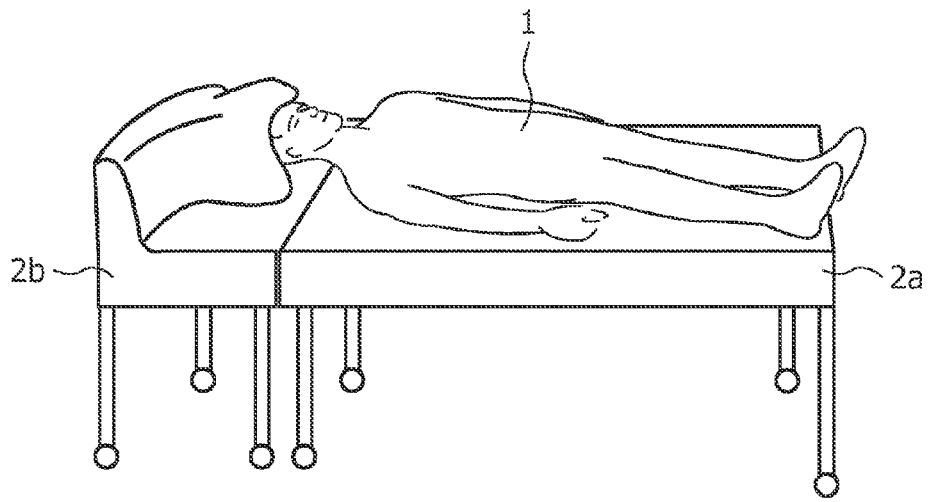

FIG. 6 schematically illustrates a first implementation of an arrangement according to the present invention. In this embodiment a part of the patient bed 2 is implemented as a kind of movable cart 2b for placement underneath a portion of the patient's body, here the head, while the main portion of the patient's body is placed on a stationary part 2a of the patient bed. The common coils of the arrangement are thus placed inside the cart, whereby the illustration of the cart 2b shown in FIG. 6 is generally to be understood as a schematic illustration. In this way, the arrangement can be made available easily by bringing it to the patient's bed 2 periodically for a monitoring period. However, the same arrangement can also be used for monitoring other patients. Further, the arrangement is built in an open fashion that does not block the patient's view and the view of medical personnel to the patient.

Figure 7:
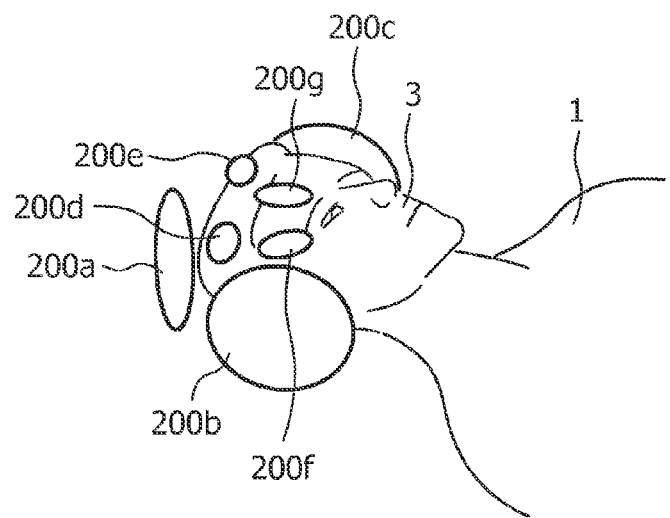

Another implementation is schematically illustrated in FIG. 7. Here, the coil array 200 comprises seven coils 200a-200g in total (just as an example) placed around a patient's head 3. The coils are arranged in such a way that they optimally fit the anatomy of the patient's head 300. Further, it is preferable to arrange the coils which shall be used as selection field coils with its symmetry axis pointing from ear to ear, i.e. horizontally, which avoids that the patient's face is covered by any coils.

Figure 8:
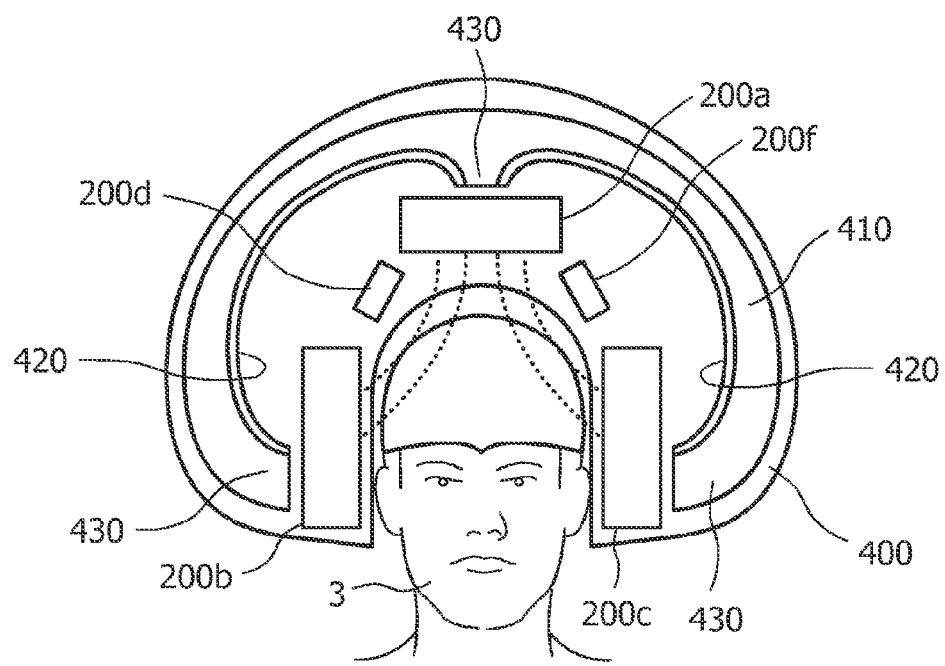

The coil arrangement can, as schematically illustrated in FIG. 8, also be implemented as a kind of helmet comprising a housing 400 within which the coils 200a-200e are placed. Further, in this embodiment the whole coil array 200 is covered and brought into connection with magnetically soft material forming a coil connector 410, said coil connector being preferably made from iron or other magnetically soft material. Further, a copper shielding 420 is provided on the coil connector 410 to prevent harmonics generation and intermodulation in the magnetically soft material due to the magnetic drive fields, to direct the magnetic flux and to increase the field strength. The shielding 420 is preferably provided around the whole coil connector 410. Preferably, as also shown in FIG. 8, the coil connector 4 is implemented such that it covers the coil array 200 like a half shell with spike-like extensions 430 connecting it to the individual coils 200a-200e for further improving the directing of the magnetic flux and increasing the field strength.

Figure 9:
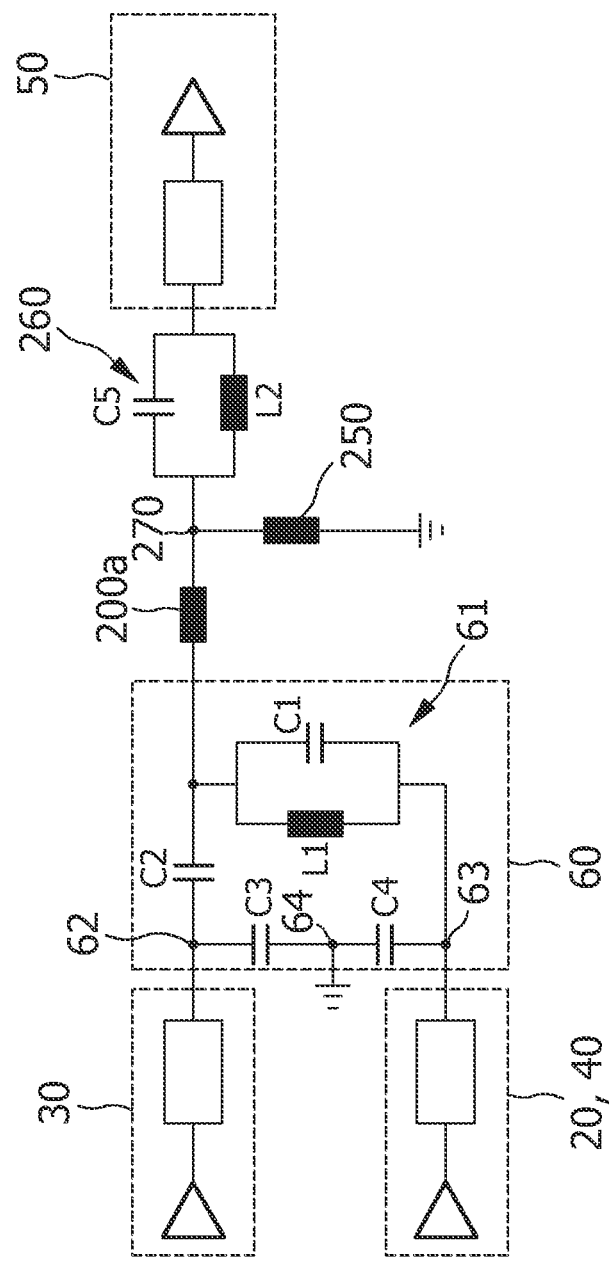
FIG. 9 shows a circuit diagram of an arrangement according to the present invention.

FIG. 9 shows an embodiment of the circuitry of the arrangement according to the present invention. In particular, a single coil 200a of the set 200 of coils is shown together with the circuitry for providing the signals for generating the magnetic field by said coil 200a as well as for receiving signals detected by said coil 200a. The diagram shows a drive field signal generating unit 30 that provides a drive field current to the coupling unit 60. Further a common selection field signal generator unit 20 and focus field signal generator unit 40 are shown which provide the selection field current and the focus field current to the coupling unit 60. Both, the selection field current and the focus field current can be provided by the same generator unit since the frequency range s of both currents are sufficiently close together.

The coupling unit 60 comprises a tank circuit 61 comprising an inductance L1 and a capacitance C1 coupled in parallel. Between the input terminal 62 for the drive field currents and the tank circuit 61 a series capacitance C2 is coupled. Further, between the input terminal 62 for the drive field currents and the input terminal 63 for the focus and selection field currents two capacitors C3 and C4 are coupled whose connecting point 64 is coupled to ground potential. This coupling makes it possible to merge the high frequency drive field signals (after suitable filtering) and the low frequency selection field and focus field signals. The tank circuit 61 mainly provides that the drive field signals are not short-cut to ground.

The circuitry of the coupling unit makes the coils resonant, and e.g. for the capacitance C4 the filter effect (as a low pass filter) is relevant. The capacitances C2 and C3 together form a matching circuit to match the impedance of the drive field signal generating unit 30 to the coil 200*a*.

For receiving detection signals another inductive element 250 is coupled in series to the coil 200*a*, whose other end is connected to ground. The tapping terminal 270 between the coil 200*a* and the inductive element 250 provides the detection signal which is provided, via a resonant circuit 260 comprising an inductive element L2 and a capacitive element C5 coupled in parallel, to the signal receiving unit 50.

It shall be noted that the focus and selection field currents can also be generated by separate generator units as depicted in FIG. 5. Further, not each of the coils of the set 200 must necessarily act as a selection field coil, drive field coil, focus field coil and/or receiving coil. It is also possible that a particular coil only has a single or some of said functions, e.g. that one coil only generates magnetic fields while another coil only receives detection signals while still another coil provides both functions. In such cases the respective parts of the circuitry can either be omitted completely or can simply not be activated and provided with the respective signals. This can, for instance, be controlled by the control unit.

It shall further be noted that according to the present invention generally only the coils for generating the magnetic fields and for signal detection need to be placed in (close) vicinity of the part of the body which shall be monitored, imaged or heated, whereas all other parts, i.e. the circuitry (in particular generator units, coupling units, processing unit, control unit, etc.), can be placed at a separate location away from the patient.

With many special applications of the present invention a spatial resolution of approximately 5 to 10 mm will be sufficient. Therefore, rather low magnetic field strengths are sufficient. For instance, a selection field having a gradient field strength of approximately 300 mT/m will be sufficient. If, as provided in a preferred embodiment, the gap between the coils used to realize the selection field, e.g. near the patient's ear, is about 200 mm, the maximum focus field strength needs to be approximately 30 mT, whereas the drive field strength can be limited to several mT. These small field strengths allow the described merging of the signals and use of a common coupling unit. Further, this minimizes heating of the neighboring portions of the patient.

Figure 10:
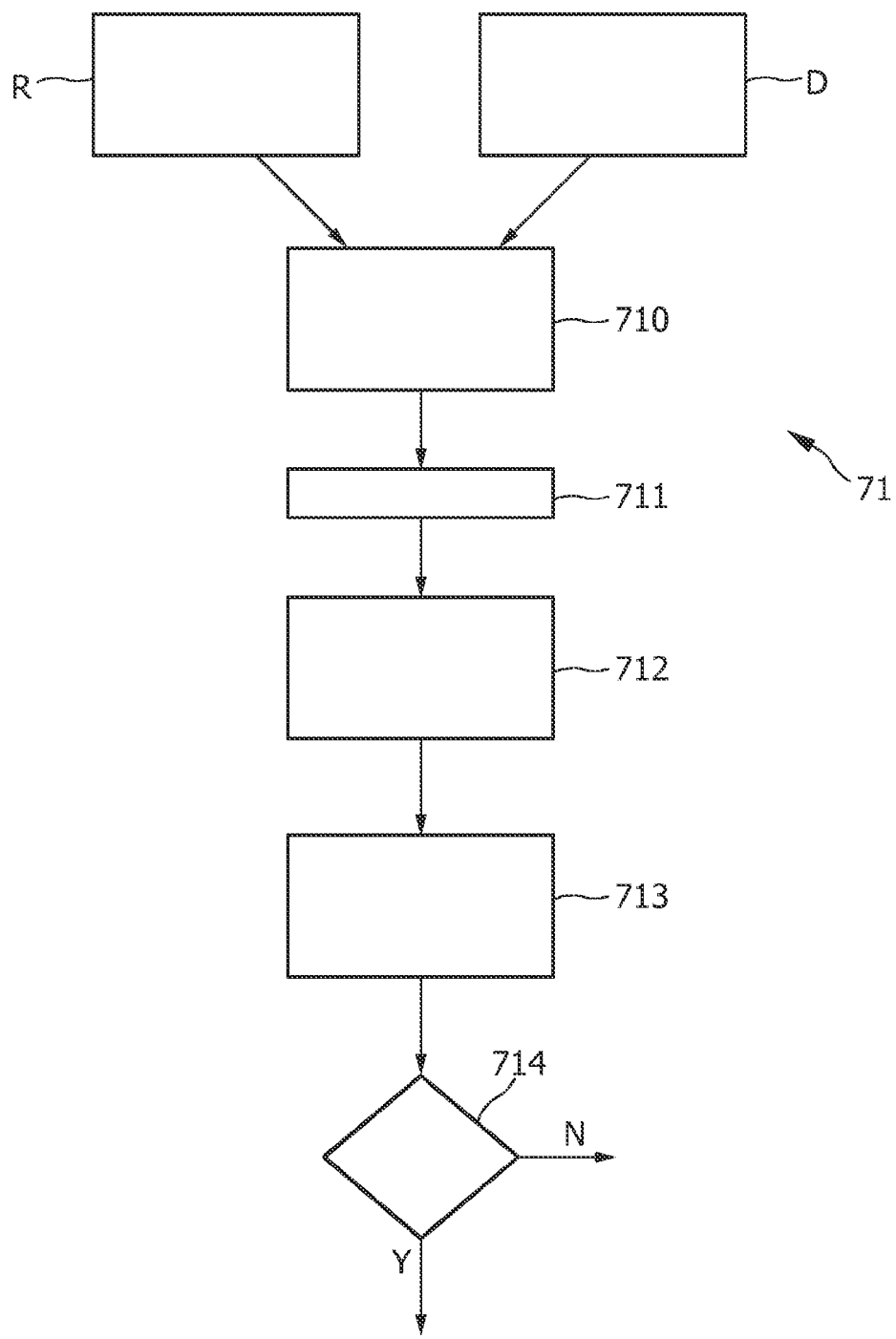
FIG. 10 shows a flow diagram illustrating a method for bleeding monitoring according to the present invention.

The general function of the filter unit and of the tank circuit is also described in WO 2008/078244 A, which discloses an arrangement for influencing and/or detecting magnetic particles, a method for calibrating such an arrangement and a method for influencing and/or detecting magnetic particles in a region of action. The arrangement particularly comprises a compensation controller providing a compensation signal to the drive signal chain and/or to the detection signal chain by means of a coupling means to enhance the signal to noise ratio. Different analog filter elements are used at the coupling means. Especially resistive coupling is used to couple a compensation signal to a drive signal chain. Three different coupling points for the compensation signal are shown as alternatives. Preferably, the point of the coupling is chosen such that at least one final passive filter stage is provided after the point of coupling An embodiment of a processing unit 71 according to the present invention is illustrated in FIG. 10. This embodiment is particularly directed to bleeding monitoring. For this purpose the processing unit 71 comprises registration means 710 for registering the present detection signals D (of the actual scans) received by the signal receiving means with reference signals R (e.g. obtained in a reference scan, for instance the first scan or an earlier scan) in order to correct for motion of the patient during signal detection or, more particularly, between detection of the detection signals D and the reference signals R. Such a registration is generally known in the art.

In a preferred embodiment the patient's head is equipped with two or more fiducial markers. At the beginning of the monitoring, the reference signals are detected, and a coordinate system is determined. During subsequent signal detections of the detection signals D, the position of the patient's head is being compared to the position during the reference signal detection by use of the fiducial markers. Of course, instead of fiducial markers it is also possible to use a large vessel (or other characteristic body parts or points) as anatomical land marks, or it is possible to use the visual impression of the patient's face, i.e. facial features are tracked using a video camera. If the patient has moved, a transformation (e.g. a rigid transformation) is being derived from the comparison of the position of the markers (or the other elements used for said purpose) and applied to the acquired detection signals to refer all signals to the same coordinate system.

Next, by comparing means 711 the local blood volume from the reference signal R is being compared to the blood volume from the (potentially motion corrected) subsequent detection signals D. Thereafter, by a first determining means 712 areas of increased blood volume are determined therein, based on said comparison. Thereafter, by use of second determining means 713, the pulsation pattern of the blood in said areas of increased blood volume are determined. Then, a decision on the presence of a bleeding can be made by a third determining means 714 by determining which of said areas of increased blood volume are areas with bleedings based on the determined pulsation pattern.

Preferably, areas of increased blood volume are determined by use of comparison of the blood volume using a certain threshold, i.e. in some regions there is considerably more blood than it has been before. Further, regions of a natural increase in blood volume, e.g. due to increased excitement or anxiety, are preferably excluded. This is done by the third determining means 714 by preferably using the fact that such regions of increased blood volume will show a characteristic pulsation pattern due to heartbeat, whereas areas with increased blood volume due to bleeding will have a different or no characteristic pulsation pattern at all. In this way, a simple and effective method for bleeding monitoring can be automatically established.

It shall be noted that the elements of the processing unit 71 can be implemented in hardware, software (e.g. as computer program run on a computer or processor) or a mixture of hardware and software.

With respect to the magnetic nano-particles which are preferably used as tracer materials, it is to be noted that magnetic materials should be used that do exhibit a sufficiently long blood retention time to allow for a subsequent scanning for a longer period of time. Alternatively, repeated small doses of magnetic materials are being injected for repeated scans. Still further, magnetic materials can be used that are embedded into red blood cells and thus circulate in the patient's blood stream, as long as those loaded red blood cells survive naturally.

Such materials are, for instance, known from A. Antonelli, C. Sfara, L. Mosca, E, Manuali, M. Magnani; New biomimetic constructs for improved in vivo circulation of superparamagnetic nanoparticles. J. Nonosci Nanotechnol, 8(5): 2270-2278, 2008. Other suitable magnetic materials are, for instance, the known materials Resovist or Feridex.

The invention can preferably be used in the medical domain, specifically in the neuro domain for stroke diagnosis and monitoring, for instance in continuous monitoring of intra-cranial and intra-cerebral bleeding, repeated, periodical monitoring of intra-cranial and intra-cerebral bleeding, imaging of the local concentration of blood in the cranial or cerebral area and/or measurement of brain perfusion. Other applications are, of course, possible as well. In particular, the present invention can also be applied for influencing magnetic particles in a region of action, in particular for heating selected parts of a patient's body (i.e. using hyperthermia, for instance to destroy cancer cells.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

Any reference signs in the claims should not be construed as limiting the scope.

The invention claimed is:

1. An arrangement (10) for influencing and/or detecting magnetic particles in a region of action (300), which arrangement comprises:
    a set (200) of common coils (200a, 200b, 200c);
    at least one selection field signal generator unit (20) for providing current to the common coils (200a, 200b, 200c) to generate a magnetic selection field (211) having a pattern in space of a magnetic field strength such that a first sub-zone (301) having a low magnetic field strength and a second sub-zone (302) having a higher magnetic field strength are formed in the region of action (300);
    at least one drive field signal generator unit (30) for providing current to the common coils (200a, 200b, 200c) to change a position of the two sub-zones (301, 302) in the region of action (300) by means of a magnetic drive field (221) so that a magnetization of a magnetic material (100) changes locally;
    at least one signal receiving unit (50) for receiving signals detected by at least common coils (200a, 200b, 200c) of said set (200) to acquire detection signals, which detection signals depend on the magnetization in the region of action (300), which magnetization is influenced by the change in the position in space of the first and second sub-zones (301, 302);
    [wherein said selection field coils, said drive friend coils and said at least one receiving coil are implemented by a set (200) of common coils (200a, 200b, 200c); and
    coupling means (60) including coupling units (60a, 60b, 60c) wherein each respective common coil (200a, 200b, 200c) of said set (200) of common coils is coupled to the selection field signal generator unit (20) and the at least one drive field generator unit (30) by a respective coupling unit of said coupling means.

2. An arrangement (10) as claimed in claim 1, wherein the common coils (200a, 200b, 200c) of said set (200) of coils are arranged in a common housing (400) including a coil connector (410) substantially made from magnetically soft material connecting said common coils (200a, 200b, 200c).

3. An arrangement (10) as claimed in claim 2, wherein said coil connector (410) comprises a shielding (420).

4. An arrangement (10) as claimed in claim 2, wherein the common coils (200a, 200b, 200c) of said set (200) of common coils, the housing (400) and said coil connector (420) are adapted for placement in close vicinity of a body part of a patient.

5. An arrangement (10) as claimed in claim 4, wherein said common coils (200a, 200b, 200c) of said set (200) of common coils, the housing (400) and said coil connector (410) are arranged in the form of a helmet for placement over a head (3) of a patient (1).

6. An arrangement (10) as claimed in claim 5, wherein said coil connector (410) is arranged in the form of a half shell covering the common coils (200a, 200b, 200c) of said set (200) of common coils and comprises extensions (430) for connection to said common coils.

7. An arrangement (10) as claimed in claim 1, further comprising focus field means comprising at least one focus field signal generator unit (40) and focus field coils (200a, 200b, 200c) for changing the position in space of the region of action (300) by means of a magnetic focus field.

8. An arrangement (10) as claimed in claim 7,
    wherein selection field coils, drive field coils, said focus field coils and at least one receiving coil are implemented by the set (200) of common coils (200a, 200b, 200c); and
    wherein said coupling unit (60a, 60b, 60c) per coil (200a, 200b, 200c) of said set (200) of common coils couples a selection field signal generator unit (20), a drive field generator unit (30) and a focus field signal generator unit (40) to one of the coils (200a, 200b, 200c) of said set (200) of common coils.

9. An arrangement (10) as claimed in claim 1, further comprising an inductive element (250) coupled in series to a receiving coil of the common coils (200a, 200b, 200c) and a resonant circuit (260) coupled between the coupling point (270) of said inductive element (250) and said receiving coil (200a) and the receiving unit (50) associated with said receiving coil (200a).

10. An arrangement (10) as claimed in claim 1, further comprising a control unit (70) for controlling said drive field signal generator units (30) such that in predetermined regions the amplitude of the generated magnetic drive field does not exceed a predetermined magnetic field intensity.

11. An arrangement (10) as claimed in claim 1 for detecting magnetic particles in a region of action (300) and for bleeding monitoring comprising:

a signal processing means (71) for processing detection signals received by the at least one signal receiving unit, said signal processing means (71) including comparing means (711) for comparing received detection signals of a region of action to previously acquired reference signals from the same region of action, first determining means (712) for determining, based on said comparison, areas of increased blood volume, second determining means (713) for determining the pulsation pattern of the blood in said areas of increased blood volume, and third determining means (714) for determining which of said areas of increased blood volume are areas with bleedings based on the determined pulsation pattern.

12. An arrangement (10) as claimed in claim 11, wherein said third determining means (714) is adapted for determining areas with no pulsation pattern or with a pulsation pattern that is not characteristic for a pulsation pattern due to heartbeat as areas with bleedings.

13. An arrangement (10) as claimed in claim 11, wherein said processing means (71) further comprises registration means (710) for registering the signals received by said at least one signal receiving unit with the reference signals for motion correction of the patient.

14. A method for influencing and/or detecting magnetic particles in a region of action (300), which method comprises the steps of:

generating a magnetic selection field (211) having a pattern in space of a magnetic field strength such that a first sub-zone (301) having a low magnetic field strength and a second sub-zone (302) having a higher magnetic field strength are formed in the region of action (300) by at least one selection field signal generator unit (20) providing current to common coils providing current to coils (200*a*, 200*b*, 200*c*)] a set (200) of common coils (200*a*, 200*b*, 200*c*);

changing the position in space of the two sub-zones (301, 302) in the region of action (300) by means of a magnetic drive field (221) from at least one drive field signal generator unit (30) providing current to the common coils (200*a*, 200*b*, 200*c*);

acquiring detection signals from at least one signal receiving unit (50) receiving signals detected by at least one common coils (200*a*, 200*b*, 200*c*) of said set coils (200), which detection signals depend on a magnetization in the region of action (300), which magnetization is influenced by the change in a position in space of the first and second sub-zones (301, 302); and each respective of common coils (200*a*, 200*b*, 200*c*) of said set (200) being coupled to the least one selection field generator unit (20) and the at least one drive field generator unit by a respective coupling unit.

15. A method as claimed in claim 14 for detecting magnetic particles in a region of action (300) and for bleeding monitoring comprising the steps of:

processing detection signals received by a signal receiving means comprising the at least one signal receiving unit (50);

comparing received detection signals of a region of action to previously acquired reference signals from the same region of action;

determining, based on said comparison, areas of increased blood volume;

determining the pulsation pattern of the blood in said areas of increased blood volume; and determining which of said areas of increased blood volume are areas with bleedings based on the determined pulsation pattern.

16. A method as claimed in claim 14, further comprising the steps of:

changing the position in space of the region of action (300) by means of a magnetic focus field generated by focus field means comprising a focus field signal generator unit (40) and focus field coils (200*a*, 200*b*, 200*c*).

17. A method as claimed in claim 16, wherein the steps of generating a magnetic selection field (211), changing the position in space of the two sub-zones (301,302) in the region of action (300) by means of a magnetic drive field (221), changing the position in space of the region of action (300) by means of a magnetic focus field generated and acquiring detection signals from at least one signal receiving unit (50) are implemented by the set (200) of common coils (200*a*, 200*b*, 200*c*); and wherein said coupling unit (60*a*, 60*b*, 60*c*) for a common coil (200*a*, 200*b*, 200*c*) of said set (200) of common coils couples a selection field signal generator unit (20), a drive field generator unit (30) and a focus field signal generator unit (40) to at least one of the common coils (200*a*, 200*b*, 200*c*) of said set (200) of common coils.

* * * * *